United States Patent [19]

Singh et al.

[11] Patent Number: 5,366,881
[45] Date of Patent: Nov. 22, 1994

[54] POLYMERIZABLE LIPIDS FOR PREPARING VESICLES THAT CONTROLLABLY RELEASE AN ENCAPSULANT

[75] Inventors: Alok Singh, Springfield; Joel M. Schnur, Burke, both of Va.

[73] Assignee: The United States of America as represented by the Secretary of the Navy, Washington, D.C.

[21] Appl. No.: 23,834

[22] Filed: Feb. 23, 1993

[51] Int. Cl.$^5$ .................. C12N 11/02; B29C 39/10; A61K 37/22; A61K 7/46
[52] U.S. Cl. .................. 435/177; 252/174.11; 252/174.12; 252/DIG. 12; 264/4; 264/4.1; 424/408; 424/450; 424/94.1; 435/4; 435/174; 435/182; 435/262.5; 435/968; 512/4; 554/1
[58] Field of Search .................. 435/4, 174, 177, 180, 435/182, 968, 262.5; 436/535; 424/94.1, 408, 417, 450; 554/1; 264/4, 4.1; 512/4; 252/174.11, 174.12, DIG. 12

[56] References Cited

U.S. PATENT DOCUMENTS

| | | | |
|---|---|---|---|
| 4,348,329 | 9/1982 | Chapman et al. | 260/403 |
| 4,900,556 | 2/1990 | Wheatly et al. | 424/450 |
| 4,933,114 | 6/1990 | O'Brien et al. | 260/403 |

*Primary Examiner*—David M. Naff
*Attorney, Agent, or Firm*—Thomas E. McDonnell; George A. Kap

[57] ABSTRACT

The present invention provides novel polymerizable lipids and mixtures thereof with non-polymerizable lipids and methods for the controlled release of encapsulated materials using stabilized or polymerized vesicles. Release is induced by pH, ions, temperature, light or other changes in the environment. Time release mechanisms are also employed. Applications of the present invention especially include encapsulation of enzymes and their subsequent sustained release for degradation of environmental pollutants, encapsulation of fluorescent markers for use in sensor systems, and encapsulation and release of fragrant molecules in detergents.

18 Claims, 2 Drawing Sheets

POLYMERIZABLE LIPIDS FOR PREPARING VESICLES THAT CONTROLLABLY RELEASE AN ENCAPSULANT

FIELD OF THE INVENTION

This invention relates to the field of lipids, and more particularly, to phospholipids.

BACKGROUND OF THE INVENTION

Research over the past 40 years has been focused on the potential for using microstructures or vesicles derived from natural and synthetic lipids for applications in areas such as encapsulation, controlled release, biosensors, enzyme immobilization, functional protein reincorporation, etc. Upon coming in contact with water, both natural and synthetic lipids self-organize such that polar hydrophilic regions (headgroups) face the aqueous medium while lipophilic portions of the assembly remain away from the aqueous medium. This process instantaneously produces closed, concentric, spherical lipid membranes called vesicles or liposomes, as well as other morphologies.

Lipid vesicles are generally made of materials having a high amphophilic lipid content, for example, surfactants or phospholipids. There are three general types of vesicles: (1) multilamellar vesicles (MLVs), which are onion-like structures having a series of substantially spherical shells formed of lipid bilayers interspersed with aqueous layers and ranging in diameter from about 0.1-4 μm, (2) large unilamellar vesicles (LUVs) which have a lipid bilayer surrounding a large, unstructured aqueous phase and have a diameter of greater than 1 μm, and (3) small unilamellar vesicles (SUVs) which are similar in structure to the LUVs except that their diameters are less than 0.2 μm. MLVs are ideal for sustained release of reactive materials, while SUVs or LUVs are required for producing stimuli responsive carriers. LUVs are most desirable for the encapsulation of large molecules such as enzymes.

A major drawback of conventional vesicles is that they are relatively unstable toward mechanical, chemical and physical perturbations and, therefore, are unsuitable for a large number of potentially important applications. Strategies for improved stability have included the incorporation of proteins, sugars, and cholesterol following the technique used for vesicle or liposome formation; i.e., well dried thin films of lipids and other material, except protein, are hydrated by addition of water or buffer and vortex mixing the mixture; protein is then added to the lipid films in hydrating buffer. However, these incorporation strategies have had only limited success.

Polymerized vesicles appear to offer a superior alternative to conventional vesicles due to the fact that it is possible to: (1) synthesize tailored molecular assemblies, (2) utilize more cost effective materials, (3) establish synthetic routes, and (4) produce bio-compatible and bio-degradable polymers. Polymerized vesicles represent a class of organic polymers that, like cell wall membranes, are capable of accommodating a wide variety of materials on the surface, in the lipophilic region, and in the central cavity. For example, the hollow cavity of a vesicle can be filled with molecules which are useful in release applications. Similarly, the membrane wall interior of a vesicle can be used for accommodating hydrophobic molecules, while the wall exterior can be used for developing strategies for target recognition and enzyme catalysis.

U.S. Pat. No. 4,900,556 to Wheatley et al. discloses preparation of vesicles (liposomes) by mixing phospholipids, such as phosphatidylcholine and phosphatidylglycerol, and cholesterol. Cholesterol is added to increase fluidity and enhance solute entrapment. The patent describes various release mechanisms such as triggering by complexation of lipids with synthetic poly(carboxylic acid) and also poly(alphaethylacrylic acid). 1,2 diretinoyl-sn-glycero-3-phosphatidylcholine, 1-palmitoyl, 2-retinoyl phosphatidylcholine and azobenzene lipid are also used in triggering liposome disruption by 360 nm light. Ion and temperature induced controlled release mechanisms are also disclosed. However, like other prior art methods, the Wheatley et al. patent release mechanisms are inefficient because the lipids utilized in the preparation of vesicles tend to be unstable and are not alone capable of forming vesicles on polymerizing.

SUMMARY OF THE INVENTION

It is an object of this invention to provide polymerizable lipids having the following structure:

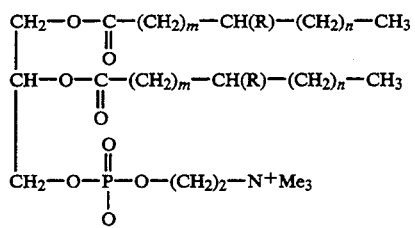

where n is 1 to 10 and m is 15-n and where each R is individually selected from the group consisting of dienyl, allyl, methacrylate, dienoate, and mixtures of such moieties.

It is another object of this invention to provide mixtures of the polymerizable and non-polymerizable lipids.

Another object of this invention is polymerized vesicles made from polymerizable lipids of this invention and mixtures thereof with non-polymerizable lipids with and without encapsulants selected from antioxidizing agents, antibacterial agents, antifungal agents, DNA, enzymes, fragrances, and fluorescent markers.

Another object of this invention is a method of controlling release of an encapsulant in vesicles made from the polymerizable and from mixtures of polymerizable and non-polymerizable lipids in response to a stimulant.

These and other objects of this invention are accomplished by making vesicles from the polymerizable lipids of this invention and from mixtures of the polymerizable and non-polymerizable lipids, encapsulating the lipids with an encapsulant selected from fragrant molecules, antioxidizing agents, antibacterial agents, antifungal agents, DNA, fluorescent molecules and enzymes and controlling release of the encapsulant in response to the stimulant.

DESCRIPTION OF THE INVENTION

Figure 1:
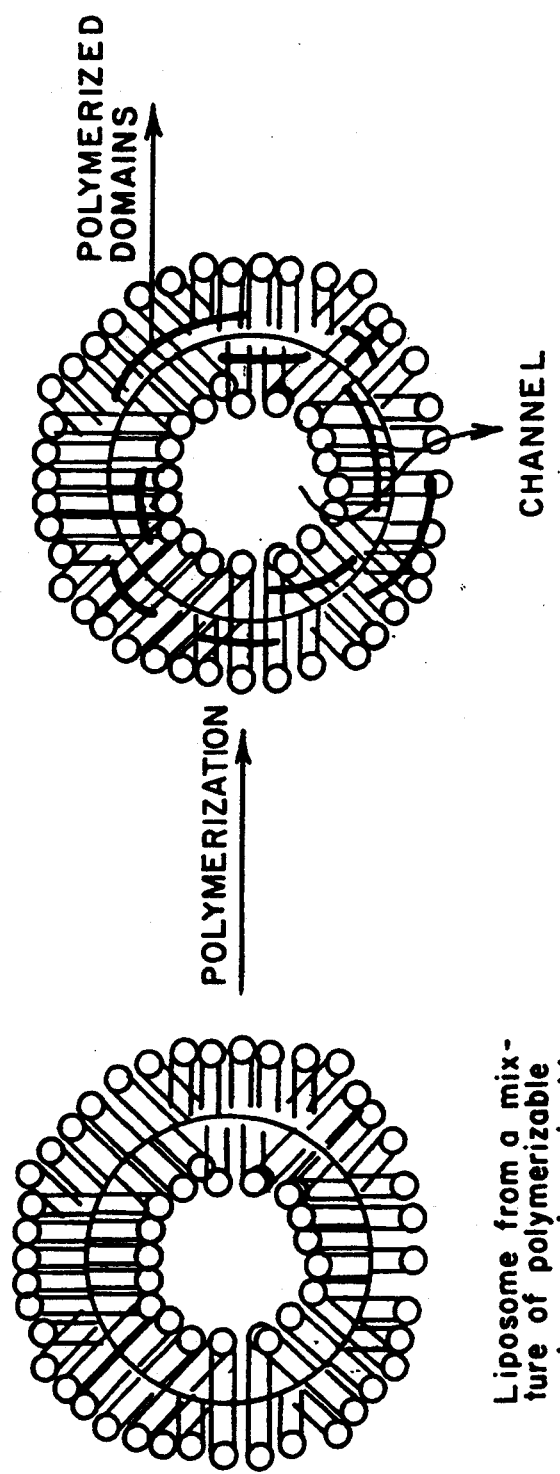
FIG. 1 shows the production of domains in polymerized vesicles or liposomes.

The present invention provides novel polymerizable lipids and mixture thereof with non-polymerizable lipids and methods for their use in controlled release applications.

In synthesizing the polymerizable lipids, acids are first synthesized in a known manner using the synthetic scheme shown below:

increasing values of n, and each R contains from 1 to 2 double bonds.

By utilizing different moieties (R) and positioning them at various sites in the acyl chain, it is possible to achieve diverse membrane properties. For example, a polymerizable moiety near the acylated carbon, i.e., as far as 6 carbon atoms away from the acyl functionality, does not perturb the membrane behavior upon polymerization. On the other hand, a polymerizable moiety at

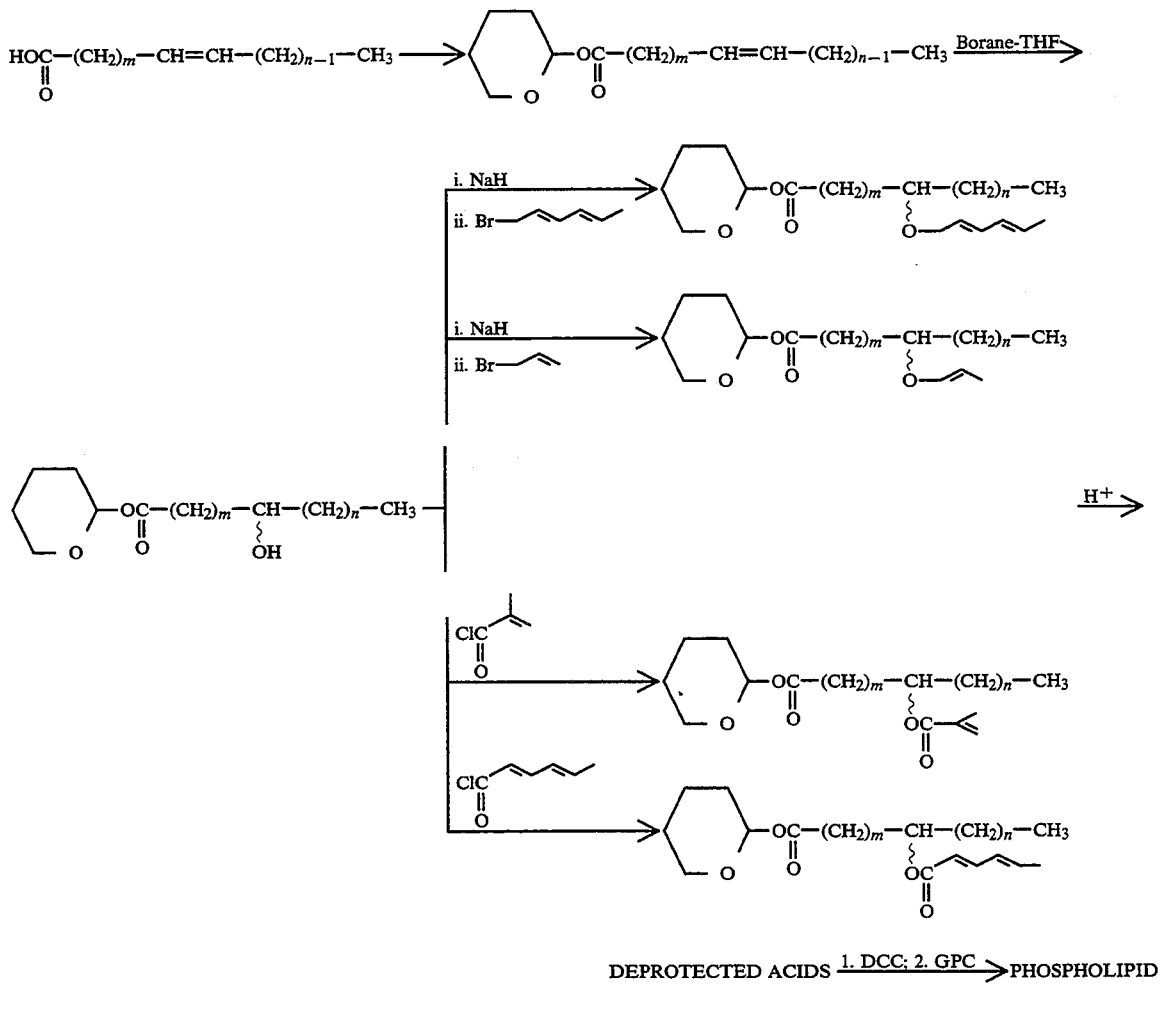

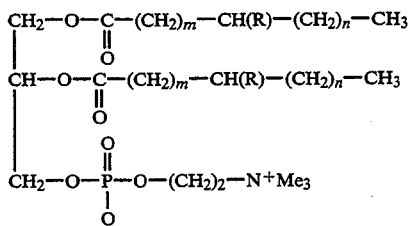

The acids are then reacted with glycerophosphorylcholine (GPC) to yield the polymerizable lipids shown below:

where n is 1 to 10, preferably 2 to 6, m is 15-n, and each R is individually selected from hydrocarbon radicals containing at least one double bond. Most preferably, n is 2 since the lipid becomes more hydrophobic with the distal part of the chain will cause fluidity in the chain since the chain mobility in lipid bilayer is high near the methyl segment. In a preferred embodiment of the invention, each R in the polymerizable lipids i.e., polymerizable phosphatidylcholines, contain dienyl (a), allyl (b), methacrylate (c), and dienoate (d) moieties having the following respective structures:

 (a),

 (b),

 (c)

and

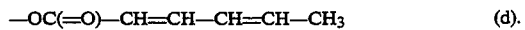 (d).

In another embodiment of this invention, polymerizable lipids of this invention, as defined above, are mixed with non-polymerizable lipids. The non-polymerizable lipids are selected from any non-polymerizable lipids, be they saturated phosphatidylcholines or other saturated lipids, although non-polymerizable phosphatidylcholines are preferred. In the mixtures, up to 90 mole percent, preferably up to 80 mole percent of the non-polymerizable lipid can be used. Examples of non-polymerizable lipids include cationic ammonium surfactants where the two alkyl chains contain 16 to 20 carbon atoms, phosphate surfactants, and saturated phospholipids or saturated phosphatidylcholines which contain the glyceryl backbone, two alkyl chains and a phosphate headgroup. Phosphate surfactants are not phospholipids because they do not contain the glyceryl backbone.

Preparation of vesicles from polymerizable lipids of this invention and mixtures of the polymerizable and non-polymerizable lipids can be made pursuant to conventional procedure. This procedure includes the steps of dissolving the lipid in a minimal amount of a solvent, evaporating the solvent to leave a layer of the lipid on interior of a container, adding water to the container to hydrate the lipid and thus form vesicles so that the ratio of lipid to water is at least about 4 mg/l, sonicating the lipid to constant turbidity at a temperature above its phase transition temperature to disperse the lipid in water and to break up the vesicles whereby the vesicles are left with a single bilayer, cooling the lipid in the form of vesicles to about room temperature, cooling to a temperature between 3° and 5° C., holding the vesicles at 3°-5° C. for about 3 hours, reheating the vesicles to above their phase transition temperature, and allowing the vesicles to cool below their crystallization temperature. The phase transition temperature of the polymerizable phospholipids of this invention is in the range of about 10° to 90° C. and that of the non-polymerizable lipids is in the range of about $-10°$ to 90° C.

The lipids of this invention can also be made by dissolving the lipid in alcohol to form an alcohol solution thereof; heating the alcohol solution to above its phase transition temperature; adding water to the alcohol solution to make a solution of water, alcohol, and lipid so that ratio of alcohol to water is about 7:3; holding this solution above its phase transition temperature for about one hour; and cooling the solution below the crystallization temperature of the lipid. In this preparation, the vesicles are made on rehydration in the alcohol-water-lipid dispersion.

Other procedures can also be used to make vesicles such as reverse phase evaporation, detergent dialysis, solvent injection techniques, and the freeze-thaw technique demonstrated in Ex. 2, herein.

Encapsulation of an encapsulant is accomplished by mixing vesicles with an encapsulant in amount of about 1 to 500% by weight, preferably 20 to 200%, based on the weight of the vesicles. The encapsulant is selected from antioxidizing agents, antibacterial agents, antifungal agents, DNA, enzymes, fragrances which may be aldehydes, and fluorescent markers. Although encapsulation or incorporation preferably precedes polymerization, it is possible to first polymerize the vesicles and then to encapsulate same. It may also be desired to remove the encapsulant from the outside surface of the of the vesicles by passing the encapsulated vesicles through a gel column or some other means.

The vesicles described herein can be polymerized by conventional photopolymerization or by free radical initiation. Polymerization of the vesicles makes them tougher and their monomeric structure is essentially retained. Polymerization of the vesicles is predominantly by photopolymerization using light of less than about 300 nm wavelength. Photopolymerization of vesicles is accomplished by exposing the vesicles to the uv light for a period of about 10 minutes to 1 hour. Free radical polymerization uses free radicals, such as AIBN. Free radical polymerization can be accomplished by mixing vesicles with about 0.01–0.5 mole/mole of a free radical material.

More specifically, uv polymerization of the vesicle dispersion can be accomplished at 254 nm (Rayonet photochemical reactor containing low pressure mercury lamps, model RPR-100) in quartz tubes contained within a thermostatic jacket. Samples can be irradiated for 2 minutes. Polymerization can be monitored by thin layer chromatography.

In polymerization by free radical initiator, typically about 0.1 mol of the initiator per mol of the polymerizable lipid is used. AIBN is the preferred initiator, although any initiator can be used.

Gamma irradiation photopolymerization can be accomplished with a $^{60}$Co source (1.33 MeV, immersed in water) for about 1260 minutes ($7.3 \times 10^6$ rads) at a rate of $0.5869 \times 10^4$/min. The temperature will typically be in the range of 4° to 18° C. during irradiation.

In the embodiment of the invention shown in FIG. 1, vesicles containing polymerizable domains are formed from a mixture of polymerizable and non-polymerizable lipids. The domains provide a means for encapsulating various encapsulants which are susceptible to stimulants to rationally control the release or to control continuous sustained release. The stimulants which can result in release of the encapsulant from vesicles include pH, ion, temperature and light. Control is effected by varying the size of the domains and the nature of the non-polymerizable lipids as well as by varying the ratio of the polymerizable lipids to the non-polymerizable lipids.

The present invention further provides methods for continuous sustained release of encapsulants is vesicles. Release rate is a function of the amount of polymerization on the vesicles i.e., there is a decreasing rate of release with increasing polymerization. Thus, time-release carriers may be created by utilizing different polymerizable lipids and by controlling the polymerization on membranes by adding non-polymerizable liplids.

Two methods which were developed to control release rate involve: (I) using a mixture of the polymerizable lipids and non-polymerizable lipids and (II) using non-polymerizable short chain spacers with polymerizable lipids. The short chain spacers are lipids which have their acyl chains cut off at the R group. In the first method (I), a non- polymerizable lipid is mixed with a polymerizable lipid whereas in the second method (II), a headgroup modified non-polymerizable lipid is mixed with a polymerizable lipid.

I. Non-Polymerizable Lipid Mixed With Polymerizable Lipid

Non-polymerizable lipid is mixed with polymerizable lipid of this invention to both reduce the relative amount of polymerizable lipid and cause the formation of the non-polymerizable lipid domains in the bilayers of vesicles. The domains of the non-polymerized lipids are then used as channels, as shown in FIG. 1, to release the entrapped contents, or encapsulants, inside the vesicles. At the chain melting temperature of a lipid, the chain order in bilayers of a vesicle becomes disrupted after the lipids are polymerized. Thus, the entrapped contents are released upon heating the lipid. The desired release temperature may be regulated by adjustment of the acyl chain length of the non-polymerizable lipids incorporated in the vesicles, since melting temperature ($T_m$) is dependent on this factor. The ratio between polymerizable and non-polymerizable lipids may be adjusted to provide additional control over the release of the encapsulants.

II. Headgroup Modified Phospholipids Mixed With Polymerizable Lipids

One or more polymerizable lipids is mixed with one or more non-polymerizable headgroup modified phospholipids including phosphatidylserine (PS) lipid, which provides an ion sensitive release system, and phosphatidylethanolamine (PE) lipid, which provides a pH sensitive release system. PS and PE lipids are commercially available. In another aspect of the embodiment of this invention, diazobenzene incorporated phosphatidylcholine lipid, which provides a light sensitive release system, is mixed with a polymerizable lipid. The systems were tested for release property as follows:

(1) With phosphatidylethanolamine (PE)

Vesicles were prepared from a mixture of non-polymerizable PE lipid and polymerizable methacrylate (Ma) lipid and encapsulated with desired fluorescent markers. While natural or synthetic PE lipid alone does not form vesicles because it does not have polymerizable capacity, it will form vesicles upon mixing with a polymerizable lipid. The mixture was then subjected to photopolymerization to polymerize only the polymerizable lipid leaving the non-polymerizable lipid intact.

(2) With phosphatidylserine (PS)

Vesicles were prepared from a mixture of non-polymerizable PS lipid and polymerizable Ma lipid and encapsulated with desired fluorescent markers. Metal ions were added to encapsulated and polymerized vesicles.

Both PS and PE lipids are known to undergo a lamellar to non-lamellar phase transition at lower pH of below about 7 and in the presence of calcium ions, respectively. Thus, the release of fluorescent dyes in the mixture of polymerizable Ma lipid and non-polymerizable PE lipid was induced by change in pH, while addition of calcium ions provided the release mechanism for the dye in the Ma-PS lipid mixture. The relative amount of PE or PS lipids provided additional control over the release time.

(3) With diazobenzene incorporated lipid

Precursor acid having the following structure:

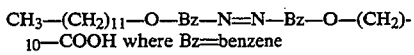

was synthesized in accordance with the synthetic scheme shown below:

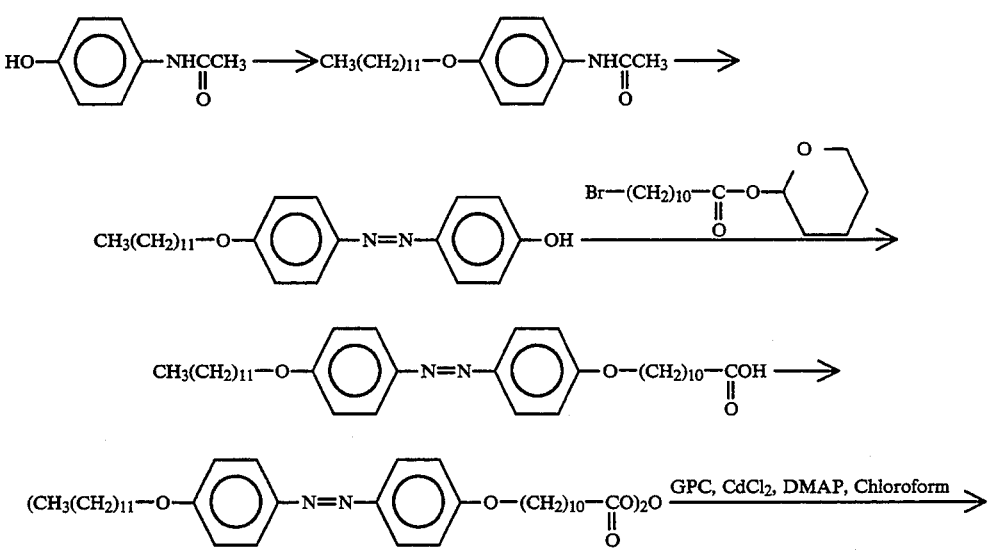

and preparation of the diazobenzene incorporated lipid, a non-polymerizable phosphatidylcholine lipid, from the acid is shown below:

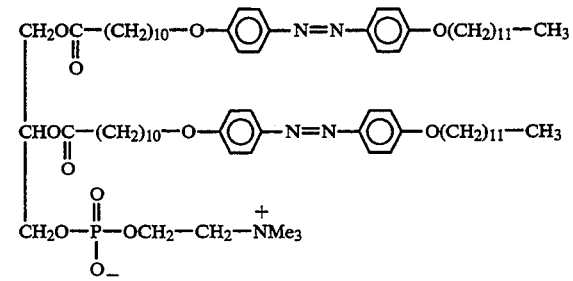

The diazobenzene incorporated lipid by virtue of its cis to trans isomerization opens or closes the release channels in bilayers of vesicles in the presence of uv light. The cis isomer has open channels whereas the trans isomer has closed channels. Trans to cis transformation can be accomplished by means of uv light of less than about 350 nm whereas cis to trans transformation can be accomplished by means of visible light of greater than about 400 nm at about room temperature.

Figure 2:
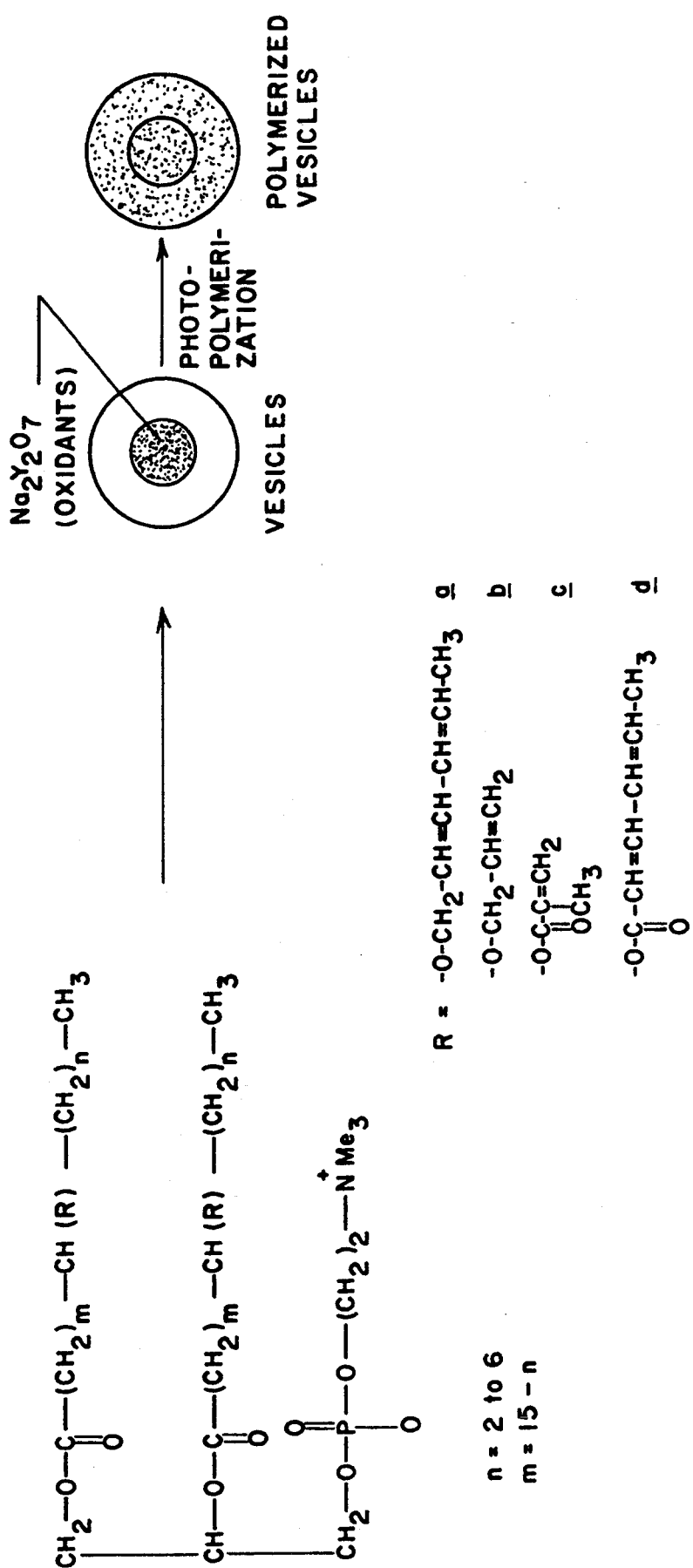
FIG. 2 shows the formation of vesicles from polymerizable lipids.

The present invention further provides methods of encapsulating encapsulants and releasing the encapsulants from vesicles made of polymerizable lipids and mixtures thereof with non-polymerizable lipids. In one embodiment of the invention, the novel polymerizable lipids of the present invention can be used alone or together with non-polymerizable lipids to form vesicles, entrap the contents, and completely polymerize the vesicles to provide a plastic bag-like structure. As shown in FIG. 2, oxidants, such as sodium dichromate and sodium hypochlorite, may be encapsulated in the vesicles and then retained by photopolymerization utilizing standard techniques. The encapsulants include antioxidizing agents, antibacterial agents, antifungal agents, DNA, enzymes, fragrances, and fluorescent markers.

In a particularly preferred embodiment, a polymerizable lipid is combined with a non-polymerizable lipid for encapsulation of lipophilic fragrant molecules in prepolymerized vesicles. The encapsulation process is accomplished by removing the non-polymerizable lipid with the aid of detergent and replacing it with fragrant molecules. Applications for the resulting polymerized vesicles include their incorporation into detergents, dryer sheets or a spray which is sprayed onto clothing. Release of the fragrant molecules can be induced by exposure to sunlight or change in body temperature while the clothing is being worn. In one embodiment, the stimulant temperature was about 100° F. and release of the fragrance was accelerated at higher temperatures.

The polymerized vesicles of the present invention have also been shown to be useful in the encapsulation of enzymes, such as proteases, which are capable of degrading environmental pollutants in the atmosphere. Generally, these enzymes cease functioning in an overwhelming concentration of pollutant. However, the present invention enables the encapsulation and subsequent controlled release of enzymes.

Yet another application of the invention is in the field of sensors, in which a sensor system which will recognize and then transduce the event. As an example, the presence of a toxin in a substance may be detected when a single molecule binds with a polymerized vesicle and triggers the release of thousands of molecules of a fluorescent dye.

EXAMPLE 1

This example demonstrates preparation of a polymerizable lipid containing a methacrylate moiety. Both of the chains in the lipid were identical steroid chains of 18 carbon atoms with the methacrylate moiety attached to the 12 carbon atom.

In this example, the precursor hydroxy carboxylic acid, 12-hydroxystearic acid, was used without any carboxylic group protection. Two grams of the hydroxystearic acid was dissolved in 40 ml dry tetrahydrofuran (THF). To this solution 790 mg of pyridine was added to it and the contents were cooled to 0° C. while keeping a positive atmosphere of nitrogen. To the resulting mixture 728 mg of methacryloyl chloride dissolved in 10 ml THF was added slowly (in about 10 minutes). A white precipitate resulted. The contents were stirred at room temperature, protected from light, for about 10 hours. The solvent was then removed under reduced pressure at 20°-25° C., and the residue was redissolved in about 80 ml ether. The ether solution was washed with 5% hydrochloric acid (twice) followed by water (twice), and dried over magnesium sulfate. The ether was removed and the residue was chromatographed on a column of silica gel (1 cm×25 cm) using chloroform-methanol (1:2) as eluant. This process yielded 2.37 g of unprotected pure acid product (1).

To make anhydride needed for making the phospholipid, 1.1 g of the unprotected acid product 1 was dissolved in 4 ml THF containing 0.5 ml triethylamine. The solution was cooled to $-23°$ C. using a carbon tetrachloride—dry ice bath and maintained at this temperature. To this, a solution of 0.65 g trichloro ethylchloroformate was added dropwise. The solution was stirred at this temperature for two hours and for one hour at room temperature. The solution then cooled to 23° C. and 1.1 g of 1 in 4 ml of THF containing 0.5 ml triethyl amine was added. The reaction was left stirring overnight letting the reaction vessel slowly attain room temperature. THF was remove from the reaction mixture and the residue was redissolved in ether and washed quickly with water to remove triethylamine and triethylamine hydrochloric complex. Ether was then removed under reduced pressure and the resulting anhydride was dried under vacuum. Yields were found to be quantitative.

1,2 Bis (12-methacryloyloxy,stearoyl) sn-glycero,3-phosphocholine, the polymerizable lipid containing methacrylate moiety, was obtained by reacting 0.3 mmol GPC cadmium chloride complex with 1.03 mmol of the anhydride of 1, in presence of 1 mmol of dimethyl aminopyridine. The reaction was carried out in freshly distilled chloroform. The resulting suspension was vigorously stirred with a teflon-coated magnetic stirring bar. The contents of the flask were then degassed with nitrogen, stoppered, protected from light and stirred for 48 hrs. at room temperature. The progress of the reaction was monitored by TLC (silica, 65:25:4, $CHCl_3:CH_3OH:H_2O$) and assumed complete when all of the lysolecithin, formed as an intermediate, had disappeared. The chloroform was removed under reduced pressure (room temperature), and the residue was dissolved in 5 ml of 4:5:1 $CHCl_3:CH_3OH:H_2O$ and passed through a column (1 cm.×17 cm.) of mixed bed resin. The column was washed with 20 mL of the same solvent. The fractions consisting of phospholipids were combined and the solvent was removed at 25° C. by applying vacuum. The vacuum-dried reaction mixture was then dissolved in a minimum volume of chloroform and further purified by chromatography using a column of silica gel (1 cm.×20 cm.). Elution was performed by using the following solvent systems in succession: Chloroform, 9:1 chloroform-methanol, 1:1 chloroform-methanol, and 1:9 chloroform-methanol. Fractions were analyzed by TLC and those fractions containing a product with an Rf identical to that of authentic DPPC were combined and the solvent was evaporated. The phospholipid was thus obtained. The pure lipid (a single spot on thin layer chromatography plates) thus obtained was yield 21%.

EXAMPLE 2

This example demonstrates the freeze-thaw technique for making vesicles.

Lipids were dispersed into a water medium by hydrating above the phase transition temperature, or lipid chain melting transition temperature, for a minimum period of 1 hour and by occasional vortex mixing. The resulting dispersion was then frozen using a dry ice-isopropanol bath and then warmed using a hot water bath. The process was repeated four times. The warm dispersion was either used as is for large MLVs, sonicated to make SUVs with high encapsulation efficiency, or sizes in a vesicle extruder.

EXAMPLE 3

This example demonstrates the use of the pH stimulant to disrupt the vesicles made from the polymerizable lipid containing the methacrylate moiety and the non-polymerizable PE lipid which is responsive to pH stimulant.

Four mg of methacryloyl phospholipid was mixed with 0.4 mg of phosphatidylethanolamine in chloroform solution (0.4 ml). The chloroform was removed under argon stream leaving a thin coating of lipid on the wall of a tube. Traces of solvent were removed by leaving the sample under high vacuum for at least two hours. The lipids in tube were then hydrated at 45° C. for an hour with pH 8.0 buffer containing 130 mM sodium chloride and 200 mM tris and 50 mM carboxyfluorescein (fluorescent dye which is self quenched at this concentration). At this concentration the dye remains self quenched. The hydrated sample was then sonicated to make small unilamellar vesicles. The vesicle dispersion was divided in two portions, one of which was polymerized by shining uv light (254 nm) for about 10 minutes. Both, polymerized and unpolymerized samples were filtered on a column of sephadex G 75-150 gel to remove exogenous fluorescent dye. The vesicles in each case were brought to pH 6.0. The pH change caused dye to release through PE molecules. The dye upon dilution became fluorescent which was checked by spectrofluorometer.

EXAMPLE 4

This example demonstrates encapsulation or incorporation of a fragrance i.e., as aldehyde, in vesicles.

Four milligrams (mg) of methacryloyl phospholipid was dissolved in chloroform solution (0.4 ml). The chloroform was removed under argon stream leaving a thin coating of lipid on the wall of a tube. Traces of solvent were removed by leaving the sample under high vacuum for at least two hours. The lipids in tube were then hydrated at 45° C. for an hour with water containing 5.0 mg of dodecaldehyde (a marker for a lipophilic fragrant molecule). The hydrated samples were then sonicated to form small unilamellar vesicles. The lipid dispersion was then divided into two portions, one of which was polymerized by uv irradiation at 254 nm for 10 minutes. The samples were then gel filtered using 1 cm×20 cm column of SEPHADEX gel (G 75-150). The presence of dodecaldehyde in gel-filtered vesicles was checked by thin layer chromatography.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A polymerizable lipid having the following structure:

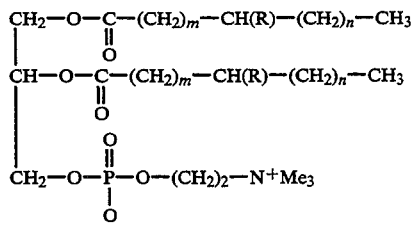

where n is 1-10 and m is 15-n; and each R is individually selected from the group consisting of:

—O—CH$_2$—CH=CH—CH=CH—CH$_3$,

—OCH$_2$CH=CH$_2$,

—OC(=O)—C(CH$_3$)=CH$_2$ and

—OC(=O)—CH=CH—CH=CH—CH$_3$.

2. The lipid of claim 1 wherein n is 2-6.

3. A mixture of polymerizable lipid and up to about 90 mole percent of non-polymerizable lipid, said polymerizable lipid having the following structure:

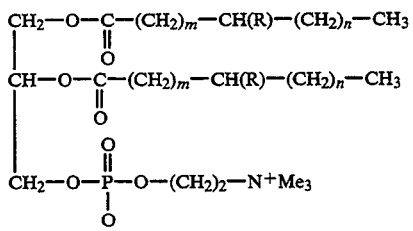

where n is 1-10 and m is 15-n; and each R is individually selected from the group consisting of:

—O—CH$_2$—CH=CH—CH=CH—CH$_3$,

—OCH$_2$CH=CH$_2$,

—OC(=O)—C(CH$_3$)=CH$_2$ and

—OC(=O)—CH=CH—CH=CH—CH$_3$.

4. The mixture of claim 3 wherein said non-polymerizable lipid is selected from the group consisting of phosphatidylserines, phosphatidylethanolamines, saturated phosphatidylcholines containing at least one diazobenzene moiety, and mixtures thereof.

5. The mixture of claim 4 wherein amount of said non-polymerizable lipid is up to about 80 mole percent.

6. Polymerized vesicles comprising polymerizable lipid or a mixture of polymerizable lipid and up to 90 mole percent of non-polymerizable lipid, said polymerizable lipid having the following structure:

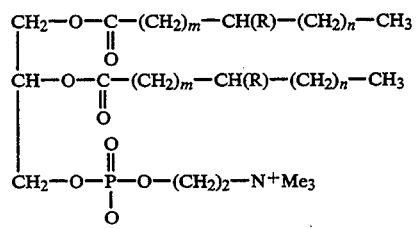

where n is 1-10 and m is 15-n; each R is individually selected from the group consisting of:

—O—CH$_2$—CH=CH—CH=CH—CH$_3$,

—OCH$_2$CH=CH$_2$,

—OC(=O)—C(CH$_3$)=CH$_2$ and

—OC(=O)—CH=CH—CH=CH—CH$_3$;

and said non-polymerizable lipid being selected from the group consisting of ammonium surfactants, phosphate surfactants, and saturated phosphatidylcholines.

7. The polymerized vesicles of claim 6 wherein n is 2–6.

8. The polymerized vesicles of claim 6 including an encapsulant selected from the group consisting of antioxidizing agents, antibacterial agents, antifungal agents, DNA, enzymes, fragrances, fluorescent markers, and mixtures thereof, said encapsulant being in an amount of 1–500% by weight of said vesicles.

9. The polymerized vesicles of claim 8 wherein amount of said encapsulant is 20–200% by weight.

10. The polymerized vesicles of claim 6 including a fragrance encapsulant in an amount of 1–500% by weight, based in the weight of said vesicles.

11. The polymerized vesicles of claim 10 wherein the fragrance encapsulant is lipophilic and is in an amount of 20–200% by weight.

12. A method of encapsulating an encapsulant in vesicles and releasing the encapsulant from the vesicles comprising the steps of:

forming vesicles from at least one lipid selected from the group consisting of polymerizable lipid and mixtures of polymerizable lipid and up to 90 mole percent of non-polymerizable lipid, based on said polymerizable lipid and said non-polymerizable lipid, said polymerizable lipid having the following structure:

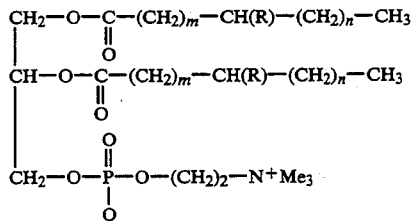

where n is 1–10 and m is 15–n; each R is individually selected from the group consisting of:

—O—CH$_2$—CH=CH—CH=CH—CH$_3$,

—OCH$_2$CH=CH$_2$,

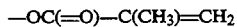

and

said non-polymerizable lipid being selected from the group consisting of ammonium surfactants, phosphate surfactants, and saturated phosphatidylcholines;

encapsulating at least one encapsulant in the vesicles in an amount of about 20–200 by weight, based on the weight of said vesicles; and subjecting the vesicles to an environmental change which causes the vesicles to release the encapsulant.

13. The method of claim 12 wherein a portion of the encapsulant is disposed on an outside surface of the vesicles and wherein the non-polymerizable lipid is selected from the group consisting of phosphatidylserines, phosphatidylethanolamines, saturated phosphatidylcholines containing at least one diazobenzene moiety, and mixtures thereof.

14. The method of claim 13 wherein the amount of said non-polymerizable lipid is up to about 80 mole percent and said method includes a step of removing said encapsulant from the outside surface of said vesicles.

15. The method of claim 12 wherein said encapsulant is selected from the group consisting of antioxidizing agents, antibacterial agents, antifungal agents, DNA, enzymes, fragrances, fluorescent markers, and mixtures thereof in an amount of 1–500% by weight of said vesicles; and wherein said saturated phosphatidylcholines contain at least one diazobenzene moiety synthesized from a precursor acid having the following structure:

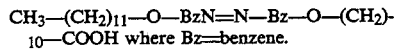

16. The method of claim 15 wherein said environmental change is selected from the group consisting of changes in temperature, pH, light and ion concentration.

17. The method of claim 16 wherein said fragrance is lipophilic.

18. The method of claim 16 wherein said fluorescent marker is a fluorescent dye.

* * * * *